US00PP30626P3

(12) United States Plant Patent
Mazzardis

(10) Patent No.: US PP30,626 P3
(45) Date of Patent: Jul. 2, 2019

(54) BLUEBERRY PLANT NAMED 'NS 14-3'

(50) Latin Name: ***Ericaceae Vaccinium* Hybrid**
Varietal Denomination: NS 14-3

(71) Applicant: Vincent David Mazzardis, Joondalup (AU)

(72) Inventor: Vincent David Mazzardis, Joondalup (AU)

(73) Assignee: Next Progeny Pty., Ltd., Subiaco (AU)

( * ) Notice: Subject to any disclaimer, the term of this patent is extended or adjusted under 35 U.S.C. 154(b) by 0 days.

(21) Appl. No.: 15/932,386

(22) Filed: Feb. 22, 2018

(65) Prior Publication Data

US 2019/0124809 P1 Apr. 25, 2019

(51) Int. Cl.
*A01H 5/08* (2018.01)

(52) U.S. Cl.
USPC ..... Plt./157

(58) Field of Classification Search
USPC ..... Plt./157
See application file for complete search history.

*Primary Examiner* — Annette H Para
(74) *Attorney, Agent, or Firm* — Randall Danskin P.S.

(57) ABSTRACT

A new and distinct variety of blueberry plant, which is denominated varietally as 'NS 14-3' is described, and which produces a fruit having a medium to large fruit size, firm fruit, a low to medium fruit acidity, and a medium to high fruit sweetness, and displaying a small dry picking scar, and a high yield, when grown under the ecological conditions prevailing near Yanchep Springs, Yanchep, Western Australia.

3 Drawing Sheets

Latin name: '*Ericaceae Vaccinium* Hybrid'.
Varietal denomination: 'NS 14-3'.

BACKGROUND OF THE NEW VARIETY

The present invention relates to a new, novel, and distinct variety of blueberry plant '*Vaccinium* Hybrid' and which has been denominated varietally as 'NS 14-3'.

ORIGIN AND ASEXUAL REPRODUCTION OF THE NEW VARIETY

The present, new variety of blueberry plant resulted from an ongoing development program of plant breeding. The purpose of this program was to improve the commercial quality of various plant varieties by creating, and releasing, promising selections of plants, including blueberries. To this end, I have made both controlled, and hybrid cross-pollinations each year to produce resulting plant populations from which improved progenies are evaluated and selected.

The blueberry plant 'NS 14-3' was derived from a controlled cross-pollination, employing the blueberry plant '7-26' (unpatented), which is the seed parent, and blueberry plant '8-10' (unpatented), which is the pollen parent, during the 2012 growing season. This first cross-pollination took place at my property, which is located at Yanchep Springs, Yanchep, Western Australia. The seed parent '7-26' is characterized, at least in part, by a semi-upright growth habit, a medium vigor, an early season ripening date, and further produces large sized, medium firmness, high sweetness, and low acidity fruit. The pollen parent '8-10', on the other hand, is characterized, at least in part, by a semi-upright growth habit, a strong vigor, an early ripening date, and further produces large sized, firm, high sweetness, and medium acidity fruit. The seed derived as a result of the first cross-pollination from the seed parent, blueberry plant '7-26', produced approximately 700 plants. These new plants were then grown at my aforementioned property, and the first fruit was evaluated during the 2014 growing season. Further, additional assessments of these same new plants, which took place in 2014 and 2015, resulted in the new variety 'NS 14-3' being selected for further asexual reproduction and evaluation. The present, new variety showed desirable traits suitable for a commercial blueberry variety. The present, new variety was asexually reproduced by cuttings, and the plants produced from this first asexual propagation were again evaluated during the 2016 and 2017 growing seasons. The asexually reproduced plants, which were produced from the aforementioned asexual reproduction process, were subsequently evaluated, and were found to be true to the original plant. It was my conclusion, at that time, that the variety 'NS 14-3' was a new, novel, and distinct variety of blueberry plant.

In relative comparison to two of the closest known varieties, that being the 'EB 9-12' blueberry plant (U.S. Plant Pat. No. 28,358), and 'EB 12-19' blueberry plant (U.S. Plant Pat. No. 27,142), the new variety of blueberry plant is clearly distinguishable. The present, new variety is distinguishable from the 'EB 9-12' blueberry plant (a closest known variety) in view of its bush, which expresses a very strong vigor when compared to the bush of the 'EB 9-12' blueberry plant, which expresses a strong to very strong vigor. Further, the present, new variety is distinguishable from the 'EB 9-12' blueberry plant in view of the fruit it produces, which possesses a medium to high fruit sweetness when compared to the fruit produced by the 'EB 9-12' blueberry plant, which produces fruit having a high to very high fruit sweetness. Still further, the present, new variety is distinguishable from the 'EB 9-12' blueberry plant (a closest known variety) in view of the fruit it produces, which possesses a firm fruit when compared to the fruit produced by the 'EB 9-12' blueberry plant, which produces a firm to very firm fruit. Additionally, the present, new variety is distinguishable from the 'EB 9-12' blueberry plant in view of the fruit it produces, which possesses a low to medium fruit acidity when compared to the fruit produced by the 'EB 9-12' blueberry plant, which produces fruit having a low fruit acidity. Moreover, the present, new variety is distinguishable from the 'EB 9-12' blueberry plant (a closest known variety) in view of the fruit it produces, which possesses a medium to large fruit size when compared to the fruit produced by the 'EB 9-12' blueberry plant, which produces fruit having a large to very large fruit size. Yet further, the present, new variety is distinguishable from the 'EB 9-12' blueberry plant in view of its bush, which produces flowers and fruit on the one-year old shoots only when compared to the bush of the 'EB 9-12' blueberry plant, which produces flowers and fruit on the current year's shoots and the one-year old shoots. Even further, the present, new variety is distinguishable from the 'EB 9-12' blueberry plant (a closest known variety) in view of its harvesting date, which is November when grown under the prevailing ecological conditions present in Yanchep Springs, Yanchep, Western Australia, when compared to the harvesting date of the 'EB 9-12' blueberry plant, which is December when grown under the same conditions present in Yanchep Springs, Yanchep, Western Australia.

The present, new variety is distinguishable from the 'EB 12-19' blueberry plant (a closest known variety) in view of its bush, which expresses a very strong vigor when compared to the bush of the 'EB 12-19' blueberry plant, which expresses a strong vigor. Further, the present, new variety is distinguishable from the 'EB 12-19' blueberry plant in view of its bush growth habit, which expresses an upright to semi-upright growth habit when compared to the growth habit of the 'EB 12-19' blueberry plant, which has a growth habit which is considered semi-upright. Still further, the present, new variety is distinguishable from the 'EB 12-19' blueberry plant (a closest known variety) in view of the fruit it produces, which possesses a medium to high fruit sweetness when compared to the fruit produced by the 'EB 12-19' blueberry plant, which produces fruit having a high to very high fruit sweetness. Additionally, the present, new variety is distinguishable from the 'EB 12-19' blueberry plant in view of the fruit it produces, which possesses a firm fruit when compared to the fruit produced by the 'EB 12-19' blueberry plant, which produces a very firm fruit. Moreover, the present, new variety is distinguishable from the 'EB 12-19' blueberry plant (a closest known variety) in view of the fruit it produces, which possesses a low to medium fruit acidity when compared to the fruit produced by the 'EB 12-19' blueberry plant, which produces fruit having a low fruit acidity. Yet further, the present, new variety is distinguishable from the 'EB 12-19' blueberry plant in view of the fruit it produces, which possesses a medium to large fruit size when compared to the fruit produced by the 'EB 12-19' blueberry plant, which produces fruit having a large to very large fruit size. Furthermore, the present, new variety is distinguishable from the 'EB 12-19' blueberry plant in view of its time of beginning of fruit ripening on one-year-old shoots, which is September when grown under the prevailing ecological conditions present in Yanchep Springs, Yanchep, Western Australia, when compared to the time of beginning of fruit ripening on one-year-old shoots of the 'EB 12-19' blueberry plant, which is August when grown under the same conditions present in Yanchep Springs, Yanchep, Western Australia. Even further, the present, new variety is distinguishable from the 'EB 12-19' blueberry plant (a closest known variety) in view of its bush, which produces flowers and fruit on the one-year old shoots only when compared to the bush of the 'EB 12-19' blueberry plant, which produces flowers and fruit on the current year's shoots and the one-year old shoots.

The present, new variety is distinguishable from the '7-26' blueberry plant (the seed parent), in view of its bush, which expresses a very strong vigor when compared to the bush of the '7-26' blueberry plant, which expresses a medium vigor. Further, the present, new variety is distinguishable from the '7-26' blueberry plant in view of its bush growth habit, which expresses an upright to semi-upright growth habit when compared to the growth habit of the '7-26' blueberry plant, which has a growth habit which is considered semi-upright. Still further, the present, new variety is distinguishable from the '7-26' blueberry plant (the seed parent) in view of the fruit it produces, which possesses a medium to high fruit sweetness when compared to the fruit produced by the '7-26' blueberry plant, which produces fruit having a high fruit sweetness. Moreover, the present, new variety is distinguishable from the '7-26' blueberry plant in view of the fruit it produces, which possesses a firm fruit when compared to the fruit produced by the '7-26' blueberry plant, which produces a fruit having a medium firmness. Yet further, the present, new variety is distinguishable from the '7-26' blueberry plant (the seed parent) in view of the fruit it produces, which possesses a low to medium fruit acidity when compared to the fruit produced by the '7-26' blueberry plant, which produces fruit having a low fruit acidity. Furthermore, the present, new variety is distinguishable from the '7-26' blueberry plant in view of the fruit it produces, which possesses a medium to large fruit size when compared to the fruit produced by the '7-26' blueberry plant, which produces fruit having a large fruit size. Even further, the present, new variety is distinguishable from the '7-26' blueberry plant (the seed parent) in view of its bush, which is evergreen when compared to the bush of the '7-26' blueberry plant, which has a bush that is semi-evergreen.

The present, new variety is distinguishable from the '8-10' blueberry plant (the pollen parent), in view of its bush, which expresses a very strong vigor when compared to the bush of the '8-10' blueberry plant, which expresses a strong vigor. Further, the present, new variety is distinguishable from the '8-10' blueberry plant in view of its bush growth habit, which expresses an upright to semi-upright growth habit when compared to the growth habit of the '8-10' blueberry plant, which has a growth habit which is considered semi-upright. Still further, the present, new variety is distinguishable from the '8-10' blueberry plant (the pollen parent) in view of the fruit it produces, which possesses a medium to high fruit sweetness when compared to the fruit produced by the '8-10' blueberry plant, which produces fruit having a high fruit sweetness. Moreover, the present, new variety is distinguishable from the '8-10' blueberry plant in view of the fruit it produces, which possesses a low to medium acidity when compared to the fruit produced by the '8-10' blueberry plant, which produces a fruit having a medium acidity. Yet further, the present, new variety is distinguishable from the '8-10' blueberry plant (the pollen parent) in view of the fruit it produces, which possesses a medium to large fruit size when compared to the fruit produced by the '8-10' blueberry plant, which produces fruit having a large fruit size. Furthermore, the present, new variety is distinguishable from the '8-10' blueberry plant in view of its time of beginning of fruit ripening on one-year-old shoots, which is September when grown under the prevailing ecological conditions present in Yanchep Springs, Yanchep, Western Australia, when compared to the time of beginning of fruit ripening on one-year-old shoots of the fruit produced by the '8-10' blueberry plant, which is October when grown in the same conditions present in Yanchep Springs, Yanchep, Western Australia. Even further, the present, new variety is distinguishable from the '8-10' blueberry plant (the pollen parent) in view of its bush, which is evergreen when compared to the bush of the '8-10' blueberry plant, which has a bush that is semi-evergreen.

BRIEF DESCRIPTION OF THE DRAWINGS

The accompanying drawings which are provided are color photographs of the new blueberry plant 'NS 14-3'.

Figure 1:
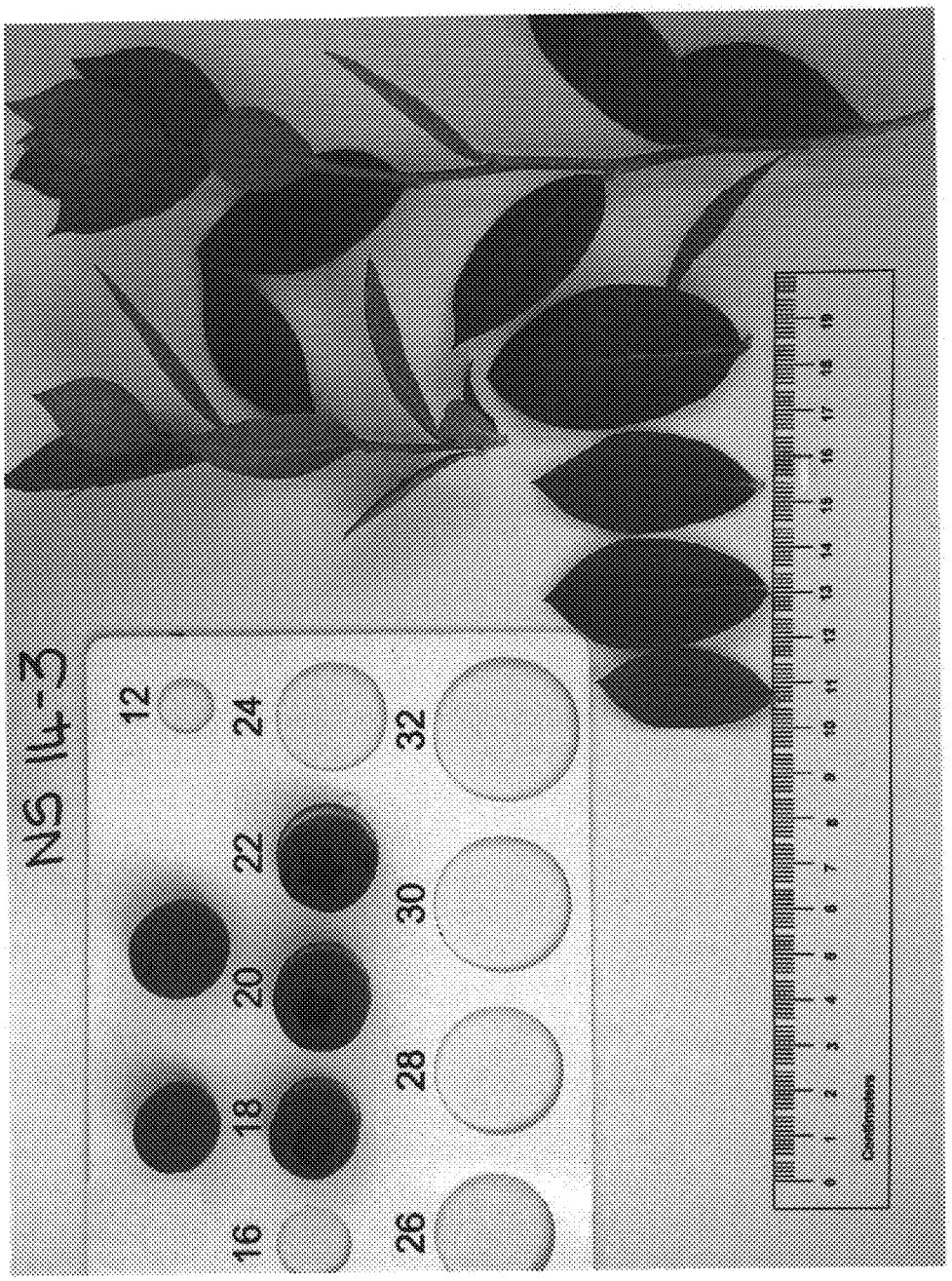
FIG. 1 is a color photograph, which shows fruit, shoots, and leaves of the new blueberry plant 'NS 14-3'. This photograph depicts several ripe fruit, which are sufficiently mature for harvesting and shipment, and further shows typical shoot-bearing leaves, and several leaves showing the dorsal and ventral colorations thereof.
Figure 2:
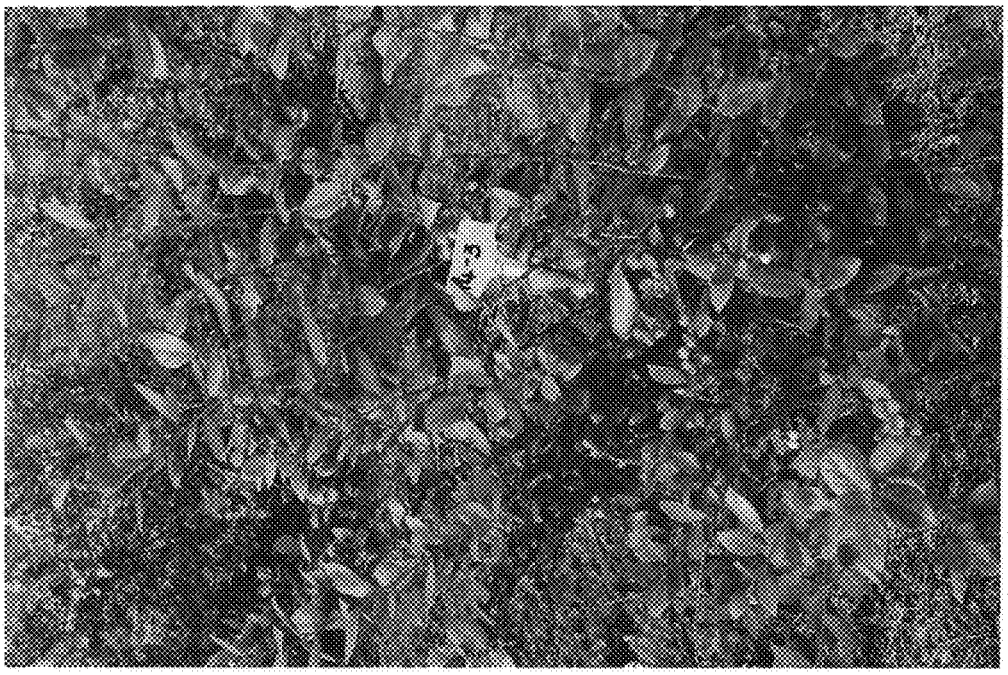
FIG. 2 is a color photograph, which shows the new blueberry plant 'NS 14-3'. This photograph depicts a mature bush with unripe fruit, and the upright to semi-upright growth habit of the new plant.
Figure 3:
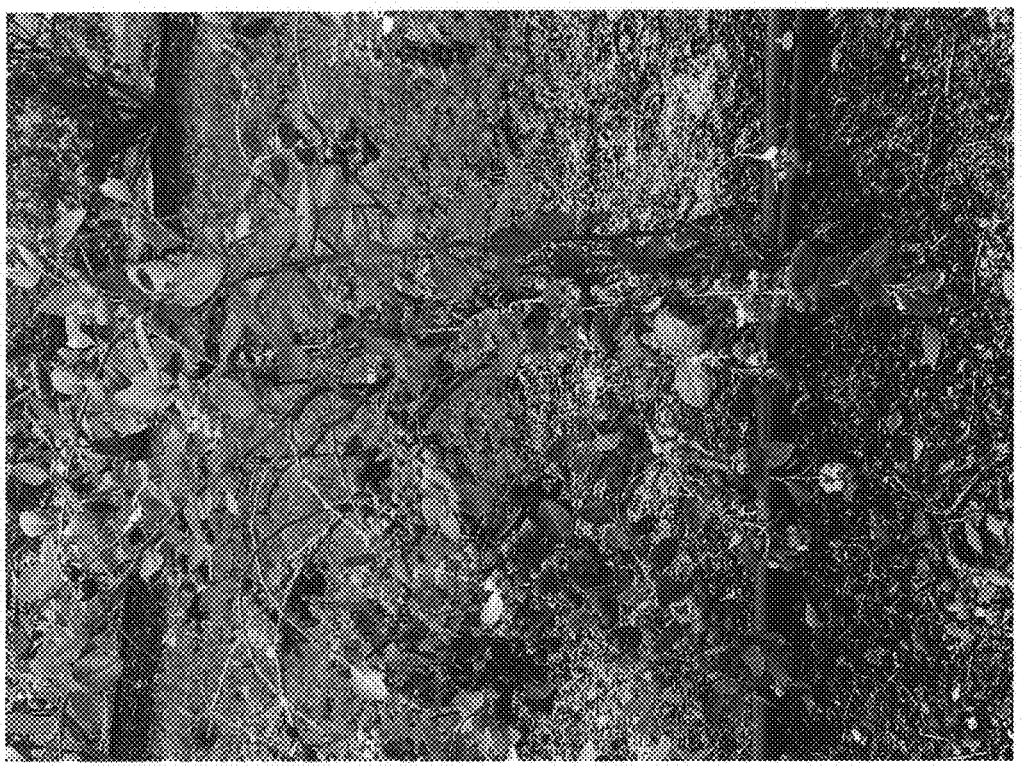
FIG. 3 is a color photograph, which shows the new blueberry plant 'NS 14-3'. This photograph depicts a mature bush with ripe and unripe fruit, the ripe fruit, as seen, are sufficiently mature for harvesting and shipment. This photograph further illustrates the medium to large fruit size and the upright to semi-upright growth habit of the new plant.

The colors in the attached photographs are as nearly true as reasonably possible in a color representation of this type. Due to chemical development, processing and printing, the leaves and fruit depicted in these photographs may or may not be accurate when compared to the actual specimens. For this reason, future color references should be made to the color plates (Royal Horticultural Society $6^{th}$ Edition, hereinafter R.H.S.), and the color descriptions as provided, hereinafter.

NOT A COMMERCIAL WARRANTY

The following detailed description has been prepared solely to comply with the provisions of 35 U.S.C. § 112, and does not constitute a commercial warranty (either expressed or implied), that the present, new variety will, in the future, display the botanical, horticultural, or other characteristics as set forth, hereinafter. Therefore, this disclosure may not be relied upon to support any future legal claims including, but not limited to, breach of warranty and merchantability, or fitness for any particular purpose, or non-infringement which is directed, in whole, or in part, to the present, new variety.

DETAILED DESCRIPTION

Referring more specifically to the botanical details of this new and distinct variety of blueberry plant, the following has been observed during the 2016 growing season under the ecological conditions prevailing at the farm of the inventor, and which is located near Yanchep Springs, Yanchep, Western Australia.

Plant:

*Plant vigor*.—Considered to be very strong for the variety.

*Plant growth habit*.—Considered to be upright to semi-upright.

*Size of plant*.—On average, about 1.5 meters by 1.0 meters.

*Internode length*.—One-Year-Old Shoots: On average, about 23.0 to 27.0 mm. This is considered to be medium to long for the variety.

*Bark color*.—Grey Red Orange (RHS 174B).

*Color, one-year-old shoots*.—Light Yellow Green (RHS 145B).

*Fruiting type*.—One-year-old shoots only.

Leaves:

*Leaf length*.—On average, about 58.5 mm. This is considered to be a medium to long length for the variety.

*Leaf width*.—On average, about 35.7 mm. This is considered to be a broad width for the variety.

*Leaf ratio, length/width*.—On average, about 1.64.

*Color of leaf, dorsal surface*.—Moderate Yellow Green (RHS 147C).

*Color of leaf, ventral surface*.—Yellow Green (RHS 147A).

*Color of leaf, vein*.—Grayish Yellow Green (RHS 148C).

*Venation pattern of leaf*.—Reticulate.

*Leaf apex texture*.—Glabrous.

*Leaf apex shape*.—Acute.

*Leaf base shape*.—Acute.

*Leaf shape*.—Elliptic.

*Leaf marginal edge*.—Entire.

*Leaf arrangement of plant*.—Alternate.

*Time of vegetative bud burst*.—This is considered to be medium for the variety. The present, new variety is considered to be evergreen.

Flowers:

*Inflorescence length, excluding peduncle*.—Considered to be medium for the variety.

*Flower bud coloration*.—The presence of anthocyanin is considered to be strong.

*Beginning of flowering on one-year-old shoots*.—June under the ecological conditions prevailing near Yanchep Springs, Yanchep, Western Australia. This is considered to be medium in the growing season for the variety.

*Beginning of flowering on current year's shoots*.—Flowering does not occur on current year shoots.

*Bloom time, duration*.—8 weeks under the ecological conditions prevailing near Yanchep Springs, Yanchep, Western Australia.

*Corolla shape*.—Urceolate.

*Corolla ridges*.—Present.

*Corolla tube size*.—Considered to be medium for the variety.

*Corolla length*.—On average, about 7.0 to 8.0 mm. This is considered to be medium for the variety.

*Corolla tube coloration*.—White (RHS 155C). The presence of anthocyanin in the corolla tube is considered to be absent to very weak.

*Pedicel color*.—Light Yellow Green (RHS 144D).

*Calyx diameter*.—On average, about 7.6 mm. This is considered to be large for the variety.

*Calyx basin depth*.—Considered to be medium for the variety.

*Attitude of sepals*.—Considered to be erect.

*Type of sepals*.—Considered to be straight.

Reproductive organs:

*Pollen anthers, color*.—Grey Orange (RHS 167C).

*Pistil, length*.—On average, about 9.2 mm.

*Pistil, color*.—Strong Yellow Green (RHS 144C).

*Pollination requirements*.—The variety is self-fertile.

Fruit:

*Unripe fruit, color*.—Light Yellow Green (RHS 145B).

*Ripe fruit skin, color*.—Bluish Black (RHS 203C).

*Ripe fruit flesh, color*.—Light Yellow Green (RHS 145D).

*Seeds, color*.—Brownish Orange (RHS N167B).

*Fruit size*.—On average, about 17.6 mm in diameter. This is considered to be medium to large for the variety.

*Fruit weight*.—On average, about 4.0 grams.

*Berry shape, longitudinal section*.—Oblate.

*Sweetness, when ripe*.—Considered to be medium to high for the variety.

*Firmness, when ripe*.—Considered to be firm for the variety.

*Acidity, when ripe*.—Considered to be low to medium for the variety.

*Cluster density*.—Considered to be medium for the variety.

*Storability of the fruit*.—Considered to be excellent for the variety.

*Market use*.—Considered to be First Grade Fresh Market Fruit.

*Beginning of fruit ripening on one-year-old shoots*.—September, under the ecological conditions prevailing near Yanchep Springs, Yanchep, Western Australia. This is considered to be medium in the season.

*Beginning of fruit ripening on current year's shoots*.—Generally, there is no fruit ripening on the current year's shoots.

*Harvesting date*.—November, under the ecological conditions prevailing near Yanchep Springs, Yanchep, Western Australia.

*Resistance to insects and diseases*.—No particular susceptibilities were noted. The present, new variety has not been tested to expose or detect any susceptibilities or resistances to any known plant and/or fruit diseases.

Although the new variety of blueberry plant possesses the described characteristics when grown under the ecological conditions prevailing near Yanchep Springs, Yanchep, Western Australia, it should be understood that the usual variations of the magnitude and characteristics incident to changes in growing conditions, fertilization, pruning, pest control, frost, climatic variables and horticultural management are to be expected.

Having thus described and illustrated my new variety of blueberry plant, what I claim is new, and desire to secure by plant Letters Patent is:

1. A new and distinct variety of blueberry plant, substantially as illustrated and described, and which is characterized principally as to novelty by producing a fruit having a medium to large fruit size, firm fruit, a low to medium fruit acidity, and a medium to high fruit sweetness, and displaying a small dry picking scar, and a high yield, when grown under the ecological conditions prevailing near Yanchep Springs, Yanchep, Western Australia.

* * * * *